United States Patent
Baldridge et al.

(10) Patent No.: US 10,981,847 B2
(45) Date of Patent: Apr. 20, 2021

(54) ISOMERIZATION AND CATALYTIC ACTIVATION OF PENTANE-ENRICHED HYDROCARBON MIXTURES

(71) Applicant: PHILLIPS 66 COMPANY, Houston, TX (US)

(72) Inventors: Anthony O. Baldridge, Bartlesville, OK (US); Neal D. McDaniel, Ochelata, OK (US); James A. Suttil, Bartlesville, OK (US); Edward C. Weintrob, Owasso, OK (US); Jianhua Yao, Bartlesville, OK (US); Bruce B. Randolph, Bartlesville, OK (US); Maziar Sardashti, Timnath, CO (US); Robert M. Walston, Skiatook, OK (US); Steven E. Lusk, Ponca City, OK (US)

(73) Assignee: Phillips 66 Company, Houston, TX (US)

( * ) Notice: Subject to any disclaimer, the term of this patent is extended or adjusted under 35 U.S.C. 154(b) by 0 days.

(21) Appl. No.: 16/593,238

(22) Filed: Oct. 4, 2019

(65) Prior Publication Data
US 2020/0109095 A1    Apr. 9, 2020

Related U.S. Application Data

(60) Provisional application No. 62/742,749, filed on Oct. 8, 2018.

(51) Int. Cl.
*C07C 5/27*     (2006.01)
*C07C 5/333*    (2006.01)
(Continued)

(52) U.S. Cl.
CPC .............. *C07C 5/2737* (2013.01); *C07C 2/76* (2013.01); *C07C 4/02* (2013.01); *C07C 5/333* (2013.01);
(Continued)

(58) Field of Classification Search
CPC ..... C07C 5/2708; C07C 5/2737; C07C 5/333; C07C 5/41; C07C 2/76; C07C 4/02;
(Continued)

(56) References Cited

U.S. PATENT DOCUMENTS

| | | | | |
|---|---|---|---|---|
| 3,699,035 A | * | 10/1972 | Hughes ................ | C10G 35/085 208/92 |
| 4,429,173 A | * | 1/1984 | Hutson, Jr. ............... | C10L 1/06 585/314 |
| 5,895,828 A | * | 4/1999 | Yao ........................ | C10G 45/64 585/418 |

* cited by examiner

*Primary Examiner* — Youngsil Jeong
*Assistant Examiner* — Jason Y Chong
(74) *Attorney, Agent, or Firm* — Phillips 66 Company

(57) ABSTRACT

The present disclosure relates to processes that catalytically convert a hydrocarbon feed stream predominantly comprising both isopentane and n-pentane to yield upgraded hydrocarbon products that are suitable for use either as a blend component of liquid transportation fuels or as an intermediate in the production of other value-added chemicals. The hydrocarbon feed stream is isomerized in a first reaction zone to convert at least a portion of the n-pentane to isopentane, followed by catalytic-activation of the isomerization effluent in a second reaction zone with an activation catalyst to produce an activation effluent. The process increases the conversion of the hydrocarbon feed stream to olefins and aromatics, while minimizing the production of C1-C4 light paraffins. Certain embodiments provide for further upgrading of at least a portion of the activation effluent by either oligomerization or alkylation.

18 Claims, 6 Drawing Sheets

(51) Int. Cl.
*C07C 4/02* (2006.01)
*C07C 2/76* (2006.01)
*C10L 1/06* (2006.01)
*C10G 63/02* (2006.01)
*C10G 63/04* (2006.01)

(52) U.S. Cl.
CPC ............ *C10G 63/02* (2013.01); *C10G 63/04* (2013.01); *C10L 1/06* (2013.01); *C07C 2521/04* (2013.01); *C07C 2529/40* (2013.01); *C10G 2300/1081* (2013.01); *C10G 2300/802* (2013.01); *C10G 2400/02* (2013.01); *C10L 2270/023* (2013.01)

(58) Field of Classification Search
CPC ... C07C 7/09; C07C 2521/04; C07C 2523/42; C07C 2527/125; C07C 2529/40; C10L 1/06; C10L 2270/023; C10G 63/02; C10G 63/04; C10G 69/10; C10G 2300/1081; C10G 2300/802; C10G 2400/02
See application file for complete search history.

ISOMERIZATION AND CATALYTIC ACTIVATION OF PENTANE-ENRICHED HYDROCARBON MIXTURES

CROSS-REFERENCE TO RELATED APPLICATIONS

This application is a non-provisional application which claims the benefit of and priority to U.S. Provisional Application Ser. No. 62/742,749 filed Oct. 8, 2018, titled "Isomerization and Catalytic Activation of Pentane-Enriched Hydrocarbon Mixtures," which is hereby incorporated by reference in its entirety.

STATEMENT REGARDING FEDERALLY SPONSORED RESEARCH OR DEVELOPMENT

None.

FIELD OF THE INVENTION

The present disclosure generally relates to processes and systems that converts at least a portion of the n-pentane in a light hydrocarbon feed stream to isopentane, followed by an activation step and subsequent upgrading to larger hydrocarbons in either an alkylation reactor or oligomerization reactor. The processes and systems produce hydrocarbons suitable for use as a blend component of a liquid transportation fuel.

BACKGROUND

A large surplus of pentanes are available in the petroleum refining industry, arising predominantly from the increased production of light hydrocarbons from U.S. shale formations, and also from limits on the quantity of volatile components that can be blended into finished transportation fuels, which must adhere to regulations on minimum vapor pressure. Unfortunately, conventional processes for upgrading light alkanes to value-added products are not well-suited for hydrocarbon feed streams that primarily comprise pentanes (i.e., isopentane and n-pentane). Therefore, it would be beneficial to find improved processes and systems for efficiently converting pentanes to more valuable products, including transportation fuels and chemicals, while minimizing the production of C1-C4 light paraffins.

The inventive processes disclosed herein provide an improved upgrading route for pentane-rich fuel blend-stocks and other pentane-rich streams that do not meet government specifications for a transportation fuel. The inventive processes and systems provide enhanced yields of upgraded products that may be suitable for use as transportation fuels or other value-added chemical products.

BRIEF SUMMARY OF THE DISCLOSURE

Certain embodiments comprise an method for converting a feed stream comprising pentanes to produce a liquid transportation fuel, the method comprising: a.) providing a hydrocarbon feed stream comprising at least 50 wt. % pentanes, including both n-pentane and isopentane; b.) contacting the hydrocarbon feed stream with one or more isomerization catalysts in a first reaction zone that is maintained at a temperature and a pressure that facilitates the isomerization of at least a portion of the n-pentane in the hydrocarbon feed stream to isopentane, thereby producing an isomerization effluent characterized by an increased ratio of isopentane to n-pentane relative to the hydrocarbon feed stream; c.) contacting the isomerization effluent with an activation catalyst in a second reaction zone that is maintained at a temperature and pressure that facilitates at least one reaction selected from dehydrogenation, cracking and aromatization, thereby converting at least a portion of hydrocarbons present in the isomerization effluent to produce an activation effluent comprising olefins containing from two to five carbon atoms, monocyclic aromatics and unconverted alkanes containing from two to five carbon atoms; d.) at least partially condensing the activation effluent to produce a liquid hydrocarbons fraction and a gaseous light hydrocarbons fraction, where the liquid hydrocarbons fraction comprises monocyclic aromatics and unreacted alkanes containing at least five carbon atoms, wherein the gaseous light hydrocarbons fraction comprises at least 80 wt. % hydrocarbons containing four or fewer carbon atoms and hydrogen.

Some embodiments further comprise separating the mixed liquid hydrocarbons into an aromatics fraction and an unreacted C5/C6 hydrocarbons fraction, where the aromatics fraction comprises monocyclic aromatics suitable for use as a blend component of gasoline and the unreacted C5/C6 hydrocarbons fraction comprises alkanes and olefins containing from five to six carbons that may be mixed with the hydrocarbon feed stream of part a.).

In some embodiments, the hydrocarbon feed stream comprises at least 5 wt. % of hydrocarbons containing four or fewer carbon atoms. In some embodiments, the hydrocarbon feed stream comprises at least 60 wt. % pentanes. In some embodiments, the hydrocarbon feed stream is contacted with one or more isomerization catalysts contained within in multiple reaction zones that are arranged in a series configuration.

In some embodiments, the activation catalyst comprises one or more zeolites characterized by Si/Al ratio ranging from 12 to 80. In some embodiments, the activation catalyst comprises ZSM-5 zeolite. In some embodiments, the activation catalyst facilitates at least one reaction selected from the group consisting of oligomerization, dehydrogenation, and aromatization.

In some embodiments, the temperature in the first reaction zone is maintained at a temperature in the range from 500° C. to 625° C. and a pressure in the range from 15 psig to 100 psig. In some embodiments, the temperature in the first reaction zone is maintained at a temperature in the range from 525° C. to 600° C. and a pressure in the range from 15 psig to 75 psig. In some embodiments, the temperature in the second reaction zone is maintained at a temperature in the range from 550° C. to 600° C. and a pressure in the range from 20 psig to 60 psig. In some embodiments, the temperature in the second reaction zone is maintained at a temperature in the range from 575° C. to 600° C. and a pressure in the range from 20 psig to 50 psig.

Some embodiments further comprise adding a diluent to at least one of the hydrocarbon feed stream and the isomerization effluent prior to the contacting with the activation catalyst, wherein the diluent is characterized as less likely to react with the activation catalyst than the hydrocarbon feed stream at the conditions of temperature and pressure that are maintained in the first reaction zone, and wherein the diluent is characterized as less likely to react with the activation catalyst than molecules present in the isomerization effluent at the conditions of temperature and pressure that are maintained in the second reaction zone.

Some embodiments further comprise adding a diluent to at least one of the hydrocarbon feed stream and the isomerization effluent prior to the contacting with the activation catalyst, wherein the diluent does not react with the isomerization catalyst at the conditions of temperature and pressure that are maintained in the first reaction zone, and wherein the diluent does not react with the activation catalyst at the conditions of temperature and pressure that are maintained in the second reaction zone. In some embodiments, the diluent is added in an amount that alters the specificity of the activation catalyst to increase the production of olefins, decrease the production of aromatics, or combinations thereof, thereby increasing the ratio of olefins to aromatics in the activation effluent. In some embodiments, the diluent is added in an amount that is effective to produce an activation effluent characterized by an olefins to aromatics ratio in the range of 0.5 to 2.0. In some embodiments, the diluent is added in an amount that is effective to produce an activation effluent characterized by an olefins to aromatics ratio in the range of 0.5 to 1.0. In some embodiments, the diluent is selected from methane, ethane, propane, butanes, and combinations thereof.

BRIEF DESCRIPTION OF THE DRAWINGS

A more complete understanding of the present invention and benefits thereof may be acquired by referring to the follow description taken in conjunction with the accompanying drawings in which.

Figure 1:
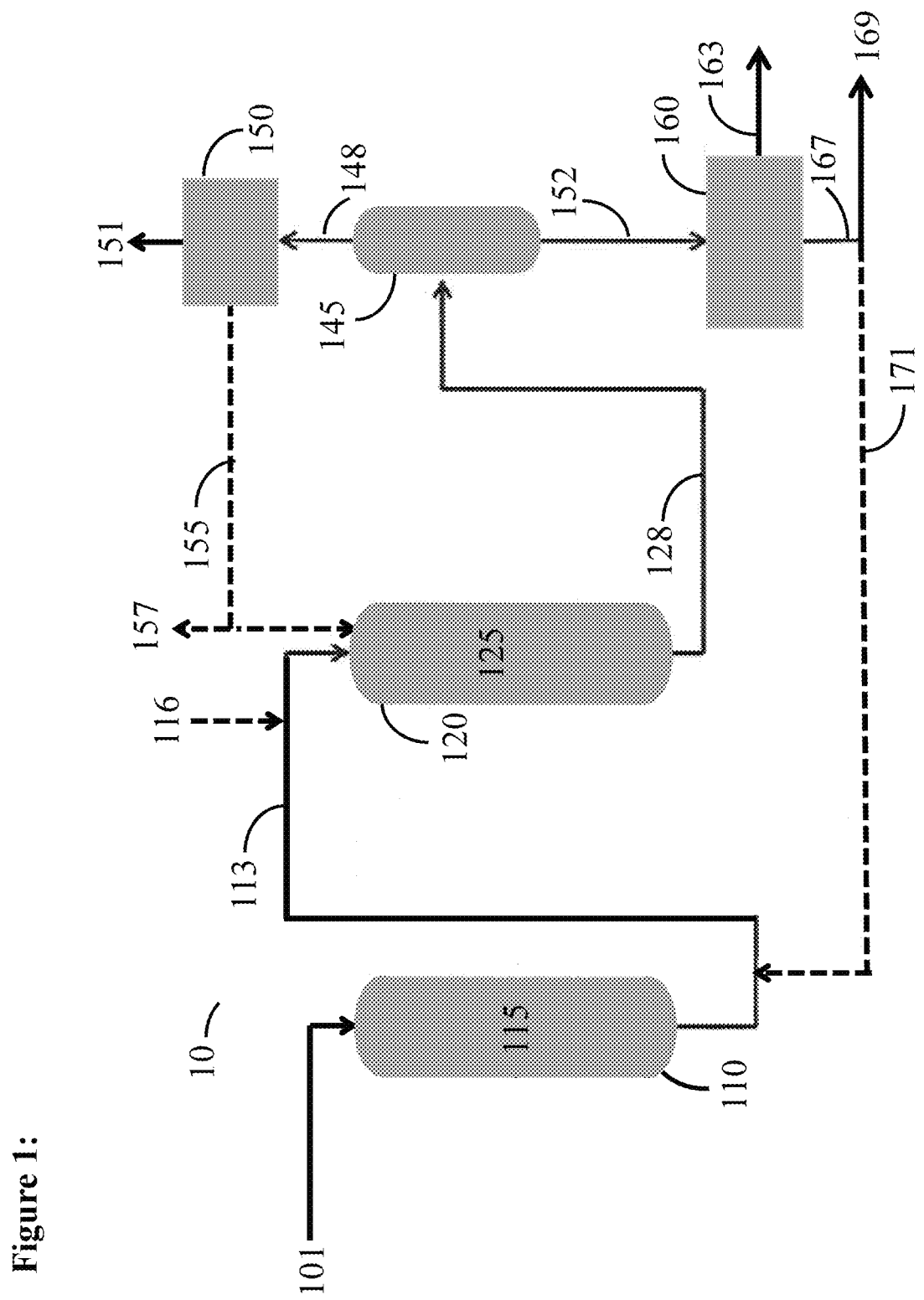
FIG. 1 is a diagram depicting a first embodiment of the inventive processes and systems.

The invention is susceptible to various modifications and alternative forms, specific embodiments thereof are shown by way of example in the drawings. The drawings may not be to scale. It should be understood that the drawings are not intended to limit the scope of the invention to the particular embodiment illustrated.

DETAILED DESCRIPTION

The present disclosure provides processes and systems for converting a mixture of light hydrocarbons to liquid transportation fuels. More specifically, it pertains to the conversion of any hydrocarbon mixture that predominantly comprises pentanes to generate upgraded products that may be sold as a value-added chemical or utilized as a blend component of a liquid transportation fuel.

Generally speaking, the inventive processes and systems described herein utilize a hydrocarbon feed stream comprising both isopentane and n-pentane and performs an initial isomerization of the hydrocarbon feed stream to convert at least a portion of the n-pentane (n-C5) in the hydrocarbon feed stream to isopentane (i-C5). The resulting isomerization effluent is then catalytically activated under conditions of temperature and pressure (typically measured at the inlet of the activation reactor) that maximize the catalytic conversion of the isomerization effluent to olefins and aromatics, while minimizing the undesirable production of C1-C4 light hydrocarbons, often referred to as fuel gas.

The resulting activation effluent is optionally further upgraded in a third reactor by contact with an oligomerization and/or alkylation catalyst at a temperature and pressure that facilitates conversion of the activation effluent to value-added chemicals and/or products suitable for use as a liquid transportation fuel blend component.

The present inventive processes and systems take advantage of the differing reactivity of pentane isomers to catalytic activation. Isopentane (i-C5) exhibits catalyst-dependent reactivity that is typically different from n-pentane (n-C5), and the optimal reactor conditions for the two isomers are therefore distinct. Experimentally, isopentane (i-C5) is more reactive than n-pentane (n-C5), and thus, can be activated at lower temperatures while maintaining high yields of desired products (such as olefins and aromatics) and decreasing the yield of C1-C4 paraffins. The inventive system takes advantage of this difference by isomerizing a portion of the n-C5 to i-C5 and n-C6 to iC6 in a first isomerization step in order to maximize both the conversion yield and selectivity of the activation step to form useful products, including (but not limited to) olefins and aromatics. Additional advantages will become evident from the detailed disclosure provided below.

As mentioned, the hydrocarbon feed stream generally comprises a stream of light hydrocarbons that comprises a mixture of pentane isomers (C5), although certain embodiments may additionally comprise C1-C4 hydrocarbons, C6-C7 hydrocarbons, or both. The hydrocarbon feed stream comprises at least 10 wt. % of a mixture of pentane isomers; optionally, at least 20 wt. %, optionally, at least 30 wt. %, optionally, at least 40 wt. %, optionally, at least 50 wt. %, optionally, at least 60 wt. %, or optionally, at least 70 wt. %. of a mixture of pentane isomers. In certain embodiments, the hydrocarbon feed stream may be obtained by processing a stream of natural gas liquids to remove lighter components (i.e., C1-C4) by way of conventional natural gas processing technologies that are well-characterized, such as de-methanizer, de-ethanizer, de-propanizer and de-butanizer fractionation columns. A typical result of such processes is commonly characterized as natural gasoline, comprising about 72 wt. % pentanes, with the remainder mostly comprising C6.

A first embodiment of the inventive processes and systems is illustrated by the process flow-diagram of FIG. 1. A hydrocarbon feed stream 101 that comprises both n-pentane and isopentane is converted in a system 10. Typically, the hydrocarbon feed stream 101 comprises at least 50 wt. % of pentane isomers, although in certain embodiments, the pentane isomers may comprise at least 60 wt. %, or at least 70 wt. % of the hydrocarbon feed stream 101. Further, the hydrocarbon feed stream 101 typically comprises less than 30 wt. %, optionally, less than 20 wt. %, optionally, less than 10 wt. % of hydrocarbons containing four or fewer carbon atoms.

The hydrocarbon feed stream 101 is received by an isomerization reactor 110 (that may optionally contain more than one isomerization catalyst, or may optionally comprise more than one isomerization reactor arranged in series configuration) that contains an isomerization catalyst 115 and comprises a first reaction zone (not depicted) that is maintained at a temperature and pressure that facilitates the isomerization of at least a portion of the n-pentane in the hydrocarbon feed stream to isopentane. The isomerization reaction occurring in the first reaction zone produces an isomerization effluent 113 that is characterized by an increased ratio of isopentane to n-pentane (relative to the corresponding ratio of the hydrocarbon feed stream 101).

Speaking generally, the isomerization process is designed for continuous catalytic isomerization of the n-pentane present in the mixture. The process is conducted in a first reaction zone that is contained within an isomerization reactor in the presence of an isomerization catalyst. The reactor maintains a partial pressure of hydrogen and operating conditions of temperature and pressure in the first reaction zone that promote isomerization while minimizing hydrocracking.

Ideally, the isomerization catalyst (or catalysts) facilitates the conversion of n-pentane to the higher octane-number isopentane, while any C6 hydrocarbons present may be converted to higher octane 2-3 dimethyl butane (and similar molecules). The isomerization reaction is equilibrium-limited. For this reason, any n-pentane that is not converted on its first pass through the isomerization reactor may optionally be recycled to the isomerization reactor, or converted in multiple isomerization reactors, arranged in series configuration, thereby further increasing the ratio of i-C5 to n-C5 in the product. The relative efficiency of separation of pentane isomers by distillation is poor. Thus, recycling may be more effectively accomplished by a molecular sieve, which selectively adsorbs n-pentane due to its smaller pore diameter relative to isopentane.

In certain embodiments, the activity of the isomerization catalyst may be decreased in the presence of sulfur, thereby decreasing the isomerization rate and, consequently, the octane number of the final product. In such embodiments, the hydrocarbon feed stream is hydrotreated to remove sulfur prior to being conveyed to the isomerization reactor.

Generally speaking, the isomerization catalyst may comprise any known isomerization catalyst. Currently, three basic families of light naphtha isomerization catalysts are known. The first are termed super-acidic catalysts (impregnated acid type), such as, for example, chlorinated alumina catalysts with platinum. Super acidic isomerization catalysts are highly active and have significant activity at temperatures as low as 265° F. (130° C.) using a lower H2/HC ratio (less than 0.1 at the outlet of the reactor). However, maintaining the high acidity of these catalysts requires the addition of a few ppm of chloriding agent to the feedstock. At the inlet of the isomerization reactor, this chloriding agent reacts with hydrogen to form HCl, which inhibits the loss of chloride from the catalyst. Unlike a zeolitic catalyst, the acidic sites on a super-acidic catalyst are irreversibly deactivated by water. These catalysts are also sensitive to sulfur and oxygenate contaminants, so the feed stream is generally hydrotreated and dried to remove residual water contamination. Commercially-available examples of chlorided-alumina catalysts include, but are not limited to, IS614A, AT-2, AT-2G, AT-10 and AT-20 (by Akzo Nobel) and ATIS-2L (by Axens). Due to their chlorinated nature, these are very sensitive to feed impurities, particularly water, elemental oxygen, sulfur, and nitrogen. When using such super-acidic catalysts, the reactor operating temperature generally ranges from 14° C. to 175° C., while the operating pressure is generally in the range from 200 psig to 600 psig, preferably in the range from 425 psig to 475 psig.

Zeolitic isomerization catalysts (structural acid type) require a higher operating temperature and are effective at isomerization at temperatures ranging from 220° C. to about 315° C., preferably at a temperature ranging from 230° C. to 275° C. Pressures utilized for isomerization with zeolitic isomerization catalysts typically range from 300 psig to 550 psig with a LHSV from 0.5 to 3.0 $hr^{-1}$. These catalysts react as bifunctional catalysts and require hydrogen at a $H_2$/HC ratio ranging from about 1.5 to about 3. Zeolitic catalysts have advantages over chlorided-alumina catalysts due to zeolitic catalyst tolerance for typical catalyst poisons sulfur, oxygenates and water. Zeolitic catalysts also do not require the injection of a chloriding agent in order to maintain catalyst activity.

A third type of conventional isomerization catalyst that may be useful in certain embodiments comprises sulfated zirconia/metal oxide catalysts. These catalysts are active at relatively low temperatures (e.g., 100° C.) with the advantage of providing enhanced isoparaffin yield. Their biggest drawback is their relative sensitivity to catalyst poisons, especially water. Certainly, other examples of isomerization catalysts that are suitable for use with the present processes and systems described herein are known by those having experience in the field, and thus, require no further disclosure here.

Again, referring to the embodiment disclosed in FIG. 1, the isomerization effluent 113 is next conveyed to an activation reactor 120 containing a first activation catalyst 125 and comprising a second reaction zone (not depicted). The activation reactor 120 is operable to maintain a temperature and pressure that is suitable to facilitate conversion of the isomerization effluent 113 to an activation effluent 128 that comprises olefins containing from two to five carbon atoms, monocyclic aromatics and unconverted alkanes containing from two to five carbon atoms.

Speaking generally, the activation catalyst may comprise a single catalyst, or a mixture of different catalysts that contacts the alkanes present in the isomerization effluent and facilitates at least one of dehydrogenation, cracking, and aromatization of the alkanes, thereby converting at least a portion of hydrocarbons present in the isomerization effluent to produce the activation effluent. Moreover, the activation effluent comprises products that may be utilized as a commodity chemical, an intermediate amenable to further catalytic upgrading, or a transportation fuel (or a component thereof).

Activation catalysts suitable for use with the processes and systems described herein may comprise any catalyst capable of cracking and/or aromatizing hydrocarbons. Favored catalysts include supported or unsupported solid acids, metals, metal chalcogenides, or metal pnictogenides, including (but not limited to) structured and amorphous silica-aluminas, structured and amorphous solid phosphoric acids, clays, other metal oxides, metal sulfates, or metal phosphates, and graphite-supported materials. In certain embodiments, ZSM-5 zeolite catalysts are utilized that are characterized by Si/Al ratios ranging from 12-80, optionally ranging from 35 to 50. Optionally, one or more elements may be impregnated on the zeolite catalyst, including one or more of Ga, Pt, Ni, Mn, Mg, Fe, Cr, P, Cu, La, Sr and F.

Generally speaking, dehydrogenation is not a prerequisite for paraffin activation in the present inventive process. A sufficient concentration of intermediate olefins can be generated through a combination of thermal dehydrogenation and catalytic cracking such that typical dehydrogenation catalyst metals (such as platinum, zinc, molybdenum, or gallium) can be avoided without significantly decreasing product yield. Conventional dehydrogenation catalysts are prone to fouling by sulfur and nitrogen contaminants that are often present in hydrocarbon feed streams derived from petroleum, so the ability to operate in the absence of these sensitive catalytic materials is highly advantageous to the process.

The inventive processes generally take advantage of the large difference in catalytic reactivity between n-C5 and i-C5. For example, utilizing a solid acid activation catalyst at temperature in excess of 550° C., the measured activation rates differ by up to 4 fold in favor of i-C5, when each isomer is contacted with the same catalyst under identical conditions (even in the same reactor simultaneously). Thus, an initial isomerization of the hydrocarbon feed stream to increase i-C5 content, followed by activating the resulting effluent in catalytic activation zone, maximize the yield of value-added, upgraded products (such as olefins and/or aromatics). Increasing conversion of pentane isomers to i-C5 also was found to unexpectedly decrease selectivity of the activation reaction to C1-C4 light gases, which typically have little value other than as fuel gas. This helps maximize the conversion of the feed to upgraded products, which is one of many advantages of the process and systems.

Table 1 (below) illustrates the difference in the activation reactivity of i-C5 versus n-C5 over a microporous silica-alumina activation catalyst. Feed streams comprising either 100 wt. % i-C5 or 100 wt. % n-C5 were each catalytically activated in separate experiments utilizing temperatures of either 600° C. or 550° C. The conversion and product distribution for i-C5 are shown in Table 1, columns 2 and 3, while similar results for the activation of n-C5 are shown in Table 1, columns 4 and 5.

TABLE 1

Product distributions for i-C5 or n-C5 isomer feed streams following conversion by a ⅛" extrudate consisting of 50 wt. % alumina binder and 50 wt. % ZSM-5 zeolite. Activation was performed by contacting the ZSM-5 catalyst with a feed stream comprising either 100 wt. % of i-C5 or 100 wt % of n-C5. Results were time-averaged over 16 hours and all reactions were performed at 1 atm with a WHSV = 4.0 $hr^{-1}$.

|  | Feed Isomer: | | | |
| --- | --- | --- | --- | --- |
|  | i-C5 | i-C5 | n-C5 | n-C5 |
| Inlet Temperature: | 600° C. | 550° C. | 600° C. | 550° C. |
| Conversion (wt. %): | 94.5 | 82.4 | 78.5 | 48.3 |
|  | Product Distribution (wt. %) | | | |
| Hydrogen | 2.4% | 1.6% | 1.1% | 0.4% |
| Methane | 9.8% | 7.8% | 5.3% | 2.3% |
| Ethane | 3.0% | 2.6% | 11.5% | 6.6% |
| Ethylene | 17.4% | 15.6% | 14.3% | 7.7% |
| Propane | 5.3% | 4.8% | 10.6% | 9.9% |
| Propylene | 21.2% | 22.1% | 16.4% | 10.3% |
| Butane | 2.9% | 4.2% | 0.8% | 1.2% |
| Butene | 8.5% | 9.9% | 5.8% | 5.5% |
| Isopentane | 5.5% | 17.6% | 0.1% | 0% |
| n-Pentane | 0% | 0% | 21.5% | 51.7% |
| Pentene | 1.2% | 1.8% | 0.8% | 1.2% |
| C6+ alkanes | 0.0% | 0.3% | 0.0% | 0.0% |
| Benzene | 4.8% | 3.3% | 4.9% | 1.0% |
| Toluene | 11.1% | 6.0% | 5.3% | 1.6% |
| Xylene | 6.4% | 2.2% | 1.3% | 0.6% |
| Ethylbenzene | 0.3% | 0.1% | 0.1% | 0.0% |
| Coke | 0.2% | 0.1% | 0.2% | 0.1% |

The data indicates that when comparing the activation of pentane isomers, conversion of i-C5 to olefins and aromatics is possible at a temperature about 50° C. less than is required for equivalent conversion of n-C5. To be clear, we observed that activation of the i-C5 feed stream at 550° C. converted about the same weight percentage of the feed stream as did activation of n-C5 at 600° C. using the same WHSV. Further, utilizing a decreased temperature of 550° C. for activation of the i-C5 feed stream advantageously decreased the production of C1-C4 light paraffins from 21.0% to 19.4% by increasing the product distribution toward olefins rather than aromatic products. Thus, the ability to separate the i-C5 isomer from n-C5 isomer (and any C6+ hydrocarbons) and activate the i-C5 enriched mixture at relatively reduced temperature, results in approximately equivalent total conversion of the overall feed stream, while decreasing the formation of undesired C1-C4 light paraffins.

Speaking generally, the temperature within the activation reactor (typically measured at, or proximal to, the inlet of the activation reactor) is maintained in the range from 500° C. to 650° C.; optionally, within the range from 525° C. to 625° C.; optionally, within the range from 525° C. to 600° C.; optionally, within the range from 550° C. to 600° C.; optionally, within the range from 550° C. to 575° C.; optionally, within the range from 575° C. to 600° C.

Referring again to the embodiment depicted in FIG. 1, the activation effluent 128 is conveyed into a first separator 145 that separates hydrogen and light hydrocarbons 148 containing four or fewer carbons from a mixed liquid hydrocarbons 152 that predominantly comprises C5 olefins, single-ring aromatics as well as unreacted pentanes and larger C6+ components originally present in the hydrocarbon feed stock 101. In certain embodiments, the first separator 145 is a two-phase splitter and separation of the activation effluent 128 is achieved by partial condensation. The light hydrocarbons 148 can be either combusted for heat generation, diverted to other upgrading processes that are outside the scope of this disclosure (not depicted), or directed to a third separator 150.

Again, referring to the embodiment depicted in FIG. 1, light hydrocarbons 148 predominantly comprises hydrogen as well as C1-C4 hydrocarbons that were not converted in the activation reactor 125. Light hydrocarbons 148 is conveyed to the third separator 150 that typically utilizes a conventional separation technology (such as, but not limited to, pressure swing adsorption technology, membrane separation technology, etc.) to separate hydrogen from the light hydrocarbons 148 to produce a hydrogen stream 151 and a C1-C4 light paraffins stream 155 that may be combusted 157 to provide at least a portion of the heat required for the process, or recycled to a point that is upstream from the activation catalyst 125 to serve as the diluent 116 that is mixed with the isomerization effluent 113.

Again, referring to the embodiment depicted in FIG. 1, the mixed liquid hydrocarbons 152 is next conveyed to a second separator 160 that in certain embodiments, may be a conventional naphtha stabilizer. Second separator 160 is operable to separate the mixed liquid hydrocarbons 152 into an aromatics fraction 163 (predominantly comprising aromatics) and an unreacted C5/C6 components fraction 167 that predominantly comprises unreacted pentanes and larger non-aromatic C6+ components. The unreacted C5/C6 components fraction 167 may be utilized directly as a gasoline blend component 169 or optionally be recycled via a C5/C6 components recycle conduit 171 and reintroduced downstream from the isomerization reactor 110.

Certain embodiments of the inventive processes and systems convey an activation effluent to an oligomerization reactor containing at least one oligomerization catalyst. The activation effluent contacts the oligomerization catalyst and is converted to larger hydrocarbon products that can be utilized as a component of a liquid transportation fuel, such as, but not limited to: gasoline, diesel and jet fuel.

Figure 2:
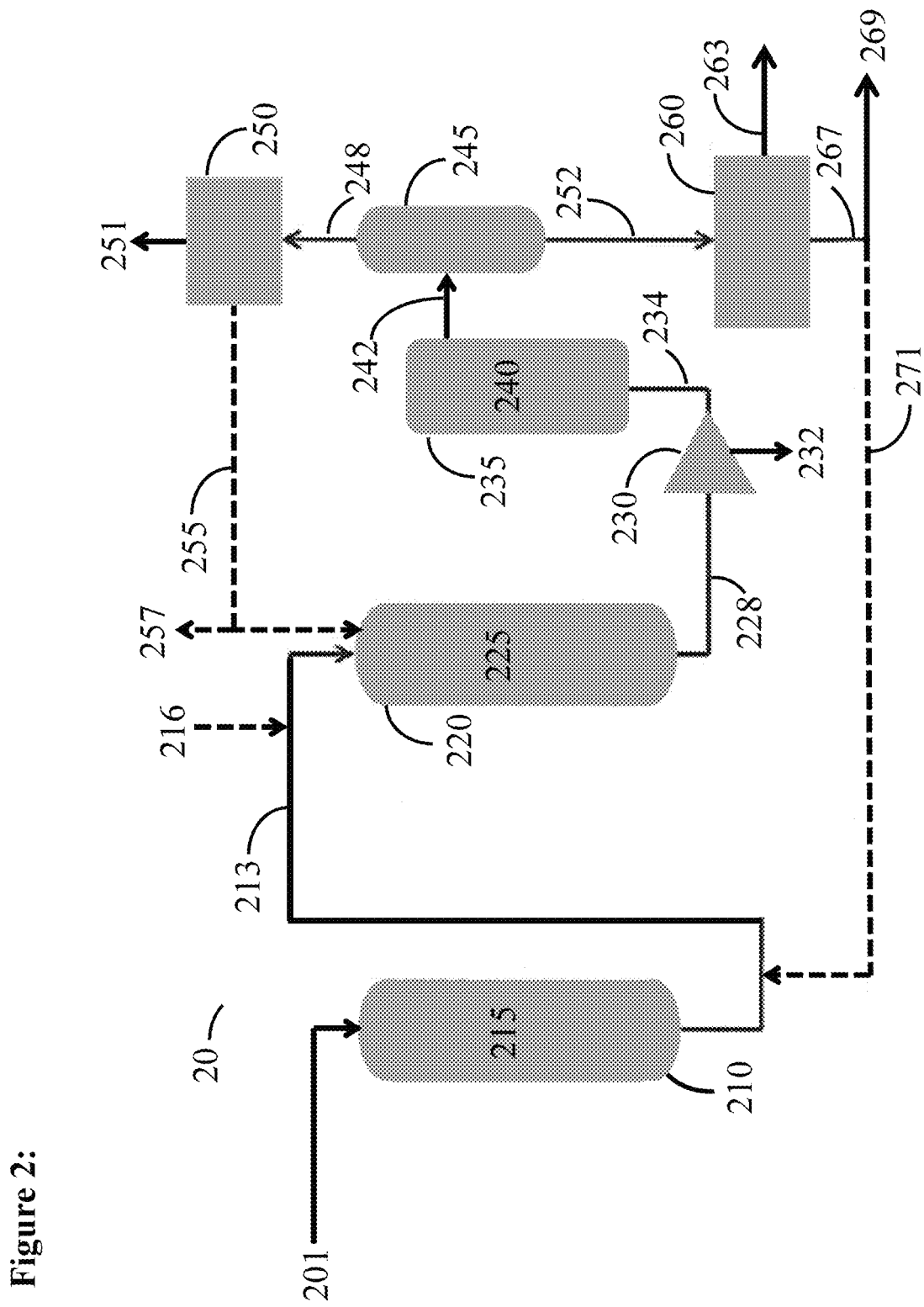
FIG. 2 is a diagram depicting a second embodiment of the inventive processes and systems.

A second embodiment of the inventive processes and systems that includes an oligomerization reactor and additional inventive features is illustrated by the process flow-diagram of FIG. 2. A hydrocarbon feed stream 201 that comprises both n-pentane and isopentane is converted in a system 20. Typically, the hydrocarbon feed stream 201 comprises at least 50 wt. % of pentane isomers, although in certain embodiments, the pentane isomers may comprise at least 60 wt. %, or at least 70 wt. % of the feed. Further, the hydrocarbon feed stream 201 typically comprises less than 10 wt. % of hydrocarbons containing four or fewer carbon atoms.

The hydrocarbon feed stream 201 is received by an isomerization reactor 210 that contains an isomerization catalyst 215 and comprises a first reaction zone (not depicted) that is maintained at a temperature (measured at the isomerization reactor inlet) and pressure that facilitates the isomerization of at least a portion of the n-pentane in the hydrocarbon feed stream to isopentane. The isomerization reaction occurring in the first reaction zone produces an isomerization effluent 213 that is characterized by an increased ratio of isopentane to n-pentane (relative to the corresponding ratio of the hydrocarbon feed stream 201). Optionally, isomerization reactor 210 may contain more than one isomerization catalyst or may optionally comprise more than one isomerization reactor arranged in series configuration (not depicted).

The isomerization effluent 213 is next conveyed to an activation reactor 220 containing a first activation catalyst 225 and comprising a second reaction zone (not depicted). The activation reactor 220 is operable to maintain a temperature and pressure that is suitable to facilitate conversion of the isomerization effluent 213 to an activation effluent 228 that comprises olefins containing from two to five carbon atoms, monocyclic aromatics and unconverted alkanes containing from two to five carbon atoms. In certain embodiments, a diluent 216 is added at any point that is upstream from, or optionally within, the activation reactor 220, but prior to contacting the activation catalyst 225. The diluent may comprise any substance that is less chemically-reactive than the constituents present in the isomerization effluent 213 at the conditions of temperature and pressure that are maintained within the activation reactor 220.

The activation effluent 228 leaves the activation reactor 220, and is conveyed to condenser 230, which may comprise one or more functions including a condenser, splitter, compressor and pump. Condenser 230 is operable to receive and condense at least a portion of the activation effluent 228 to produce a liquid hydrocarbons 232 comprising C6 and larger hydrocarbons including paraffins, olefins and aromatics and a (gas phase) light activation effluent 232 (not depicted) comprising C1-C5 alkanes and olefins. The liquid hydrocarbons 232 are removed, while the light activation effluent compressed in the condenser 230 to produce a compressed activation effluent 234 that is next conveyed to an oligomerization reactor 235 that contains an oligomerization catalyst 240 and comprises a second reaction zone (not depicted).

Speaking generally, the oligomerization catalyst may comprise any solid catalyst (or mixture of catalysts) characterized as possessing either Brønsted or Lewis acidic properties. In certain embodiments, the oligomerization catalyst is a zeolite or mixture of zeolites, or a reactive transition metal oxide. In certain embodiments, the oligomerization catalyst is ZSM-5, although many zeolites are well-characterized as possessing oligomerization properties and may be suitable for use (either alone or in combination) with the inventive processes and systems described herein.

Other well-characterized oligomerization catalysts include, but are not limited to: nickel oxides, aluminum alkyls, aluminum halides, perfluoroaryl boranes, oligomeric methyl aluminoxanes (including supported), perfluoroaryl boranes, fluoroarylanes, trityl borate, ammonium borate (and aluminate salts thereof), supported $PhNMe_2H+B(C6F5)4-$ and borate anions and superacidic solid Brønsted acids, among others.

Speaking generally, the oligomerization reactor is maintained at a temperature and pressure suitable to facilitate oligomerization of olefins present in the gaseous activation effluent, thereby producing larger hydrocarbons comprising at least six carbons that are preferably characterized by a boiling point that is in the boiling point range of a liquid transportation fuel (e.g., gasoline or diesel). The oligomerization reactor is generally maintained at a total pressure in a range from 14 psia to 800 psia, optionally in the range from 50 psia to 300 psia. The oligomerization reactor is typically maintained at a temperature (measured within the oligomerization reactor inlet) in the range from 200° C. to 420° C., optionally in the range from 200° C. to 350° C. Typically, flow thorough the oligomerization reactor is maintained at a weight hourly space velocity (WHSV) in the range from 0.5 $hr^{-1}$ to 10 $hr^{-1}$. Optionally, the WHSV is in the range from 0.5 $hr^{-1}$ to 2.0 $hr^{-1}$. While higher overall throughput is desirable, ideally the chosen WHSV allows for conversion of at least 85% of hydrocarbons present in the gaseous activation effluent at the selected operating temperature and pressure.

The catalytic conversion occurring in the oligomerization reactor produces an oligomerization effluent that typically comprises an increased quantity of hydrocarbon molecules that are characterized by a boiling-point in the range of a liquid transportation fuel (e.g., gasoline and diesel). Preferably, the combination of isomerization, activation and oligomerization converts at least 30 wt % of the original feed stream to hydrocarbon molecules that are characterized by a boiling point that is in the range of gasoline.

Referring again to the embodiment depicted in FIG. 2, the oligomerization effluent 242 produced in the second reaction zone (not depicted) that is contained within the oligomerization reactor 235 is conveyed to a first separator 245 that separates the oligomerization effluent 242 into two fractions: a light hydrocarbons fraction 248 comprising C1-C4 hydrocarbons and hydrogen, and a heavy hydrocarbons fraction 252 comprising hydrocarbons containing at least five carbon atoms (C5+) that may be utilized directly as a blend component of a liquid transportation fuel or an intermediate product that may be additionally processed prior to blending into a liquid transportation fuel.

In the embodiment depicted in FIG. 2, the heavy hydrocarbons fraction 252 is conveyed to a second separator 260 that is optionally a naphtha stabilizer. The second separator 260 is operable to remove an olefins fraction 267 comprising predominantly alkanes and olefins containing five to six carbon atoms from the condensed liquid hydrocarbons 252 in order to decrease Reid vapor pressure and increase octane rating of the resulting liquid hydrocarbon product 263, which predominantly comprises hydrocarbon molecules that are characterized by a boiling-point in the range of a liquid transportation fuel, such as, but not limited to, gasoline, diesel and jet fuel. The olefins fraction 267 may be used directly as a blend component 269 of a liquid transportation fuel or is optionally mixed with hydrocarbon feed stream 201 at a point that is downstream from the isomerization reactor 210. This recycling not only increases the overall yield of fuel-range products, but also serves as a route to indirectly recycle any benzene present in the olefins fraction 267 to the alkylation reactor 240, as any such benzene would be relatively unreactive in the isomerization reactor 210 and activation reactor 220. Optionally, a portion of the liquid hydrocarbons 231 derived from the condenser 230 may be combined with the liquid hydrocarbon product 263.

Speaking generally, in certain embodiments, the liquid hydrocarbon product of the process may be hydrotreated in a hydrotreating reactor containing a hydrotreating catalyst in order to reduce olefin and aromatic content in the liquid hydrocarbon product, as well as to remove nitrogen-containing and sulfur-containing compounds. The hydrotreating reactor contains at least one hydrotreating catalyst (such as, for example, NiMo, CoMo, etc.) or a precious metal catalyst (such as $Pt/Al_2O_3$, $Pd/Al_2O_3$, or Pd/C, etc) and is maintained at a pressure and temperature suitable for facilitating hydrotreating catalytic reactions. Such processes are conventional in nature and therefore will not be described in greater detail here.

Again, referring to the embodiment depicted in FIG. 2, light hydrocarbons fraction 248 predominantly comprises hydrogen as well as C1-C4 hydrocarbons that remained unconverted in the oligomerization reactor 240. Light hydrocarbons fraction 248 leaves the first separator 245 and is optionally conveyed to a third separator 250 that utilizes a conventional separation technology (such as, but not limited to, pressure swing adsorption technology, membrane separation technology, etc.) to separate hydrogen from the light hydrocarbons to produce a hydrogen stream 251 and a C1-C4 light paraffins stream 255 that may be combusted 257 to provide at least a portion of the heat required for the process, or recycled to a point that is upstream from the activation catalyst 225 to serve as the diluent 216 that is mixed with the isomerization effluent 213.

Certain embodiments of the inventive processes and systems convey the activation effluent to an aromatic alkylation reactor containing at least one alkylation catalyst. This produces larger hydrocarbon products that can be utilized as either gasoline or diesel transportation fuel, or a component thereof.

Figure 3:
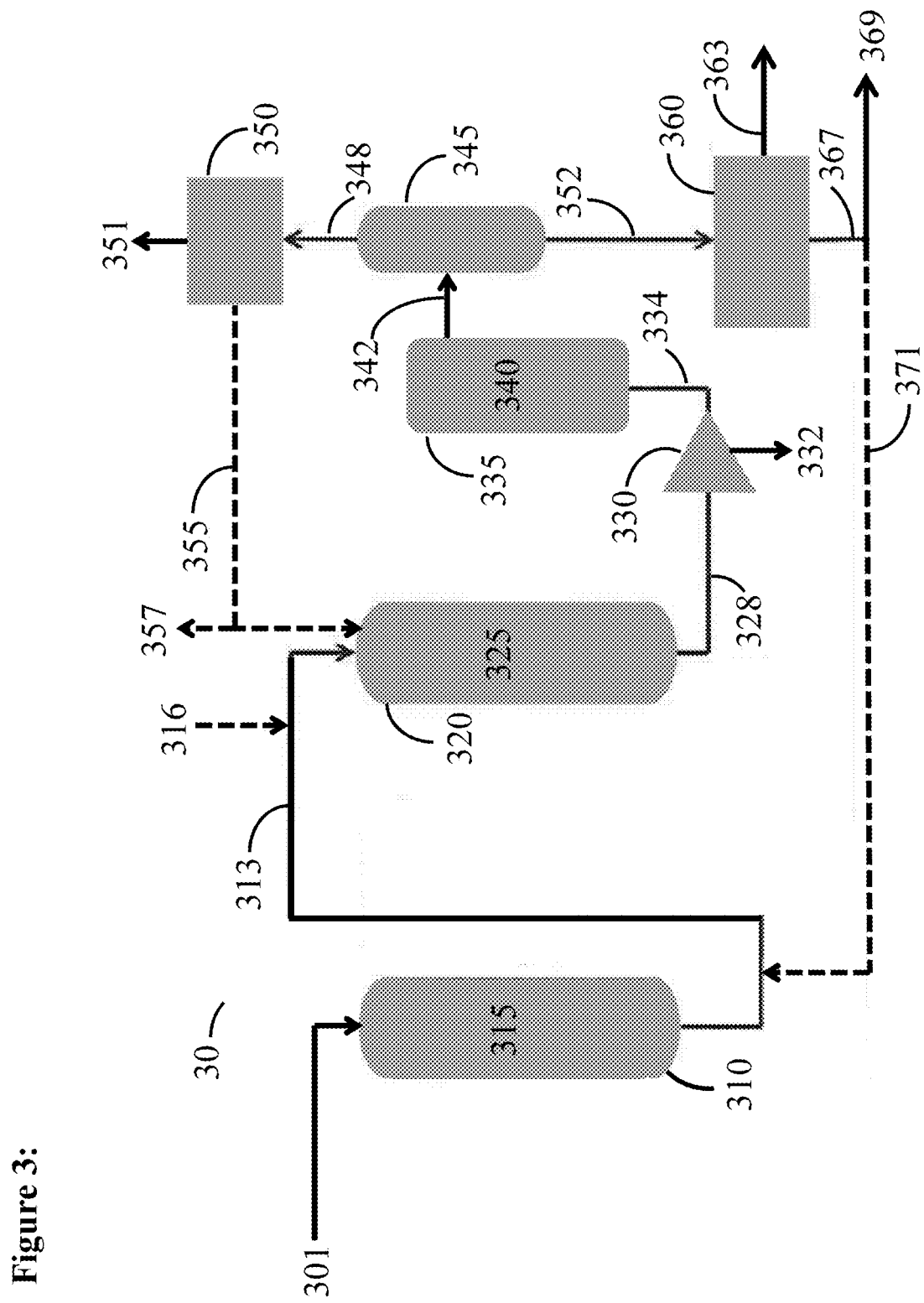
FIG. 3 is a diagram depicting a third embodiment of the inventive processes and systems.

A third embodiment of the inventive processes and systems that includes an alkylation reactor and additional inventive features is illustrated by the process flow-diagram of FIG. 3. A hydrocarbon feed stream 301 that comprises both n-pentane and isopentane is converted in a system 30. Typically, the hydrocarbon feed stream 301 comprises at least 50 wt. % of pentane isomers, although in certain embodiments, the pentane isomers may comprise at least 60 wt. %, or at least 70 wt. % of the feed. Further, the hydrocarbon feed stream 301 typically comprises less than 10 wt. % of hydrocarbons containing four or fewer carbon atoms.

The hydrocarbon feed stream 301 is received by an isomerization reactor 310 that contains an isomerization catalyst 315 and comprises a first reaction zone (not depicted) that is maintained at a temperature (measured at the isomerization reactor inlet) and pressure that facilitates the isomerization of at least a portion of the n-pentane in the hydrocarbon feed stream to isopentane. The isomerization reaction occurring in the first reaction zone produces an isomerization effluent 313 that is characterized by an increased ratio of isopentane to n-pentane (relative to the corresponding ratio of the hydrocarbon feed stream 301). Optionally, isomerization reactor 310 may contain more than one isomerization catalyst or may optionally comprise more than one isomerization reactor arranged in series configuration (not depicted).

The isomerization effluent 313 is next conveyed to an activation reactor 320 containing a first activation catalyst 325 and comprising a second reaction zone (not depicted). The activation reactor 320 is operable to maintain a temperature and pressure that is suitable to facilitate conversion of the isomerization effluent 313 to an activation effluent 328 that predominantly comprises olefins containing from two to five carbon atoms, monocyclic aromatics and unconverted alkanes containing from two to five carbon atoms. In certain embodiments, a diluent 316 is added at any point that is upstream from, or optionally within, the activation reactor 320, but prior to contacting the activation catalyst 325. The diluent may comprise any substance that is less chemically-reactive than the constituents present in the isomerization effluent 313 at the conditions of temperature and pressure that are maintained within the activation reactor 320.

The activation effluent 328 leaves the activation reactor 320, and is conveyed to condenser 330, which may comprise one or more functions including a condenser, splitter, compressor and pump. Condenser 330 is operable to receive and condense at least a portion of the activation effluent 328 to produce a liquid hydrocarbons (332) comprising C6 and larger hydrocarbons including paraffins, olefins and aromatics, and a (gas-phase) light activation effluent 332 not depicted) comprising C1-C5 alkanes and olefins. The liquid hydrocarbons 332 are removed, while the light activation effluent is compressed in the condenser 330 to produce a compressed activation effluent 234 that is next conveyed to an alkylation reactor 335 that contains an alkylation catalyst 340 and comprises a second reaction zone (not depicted).

Speaking generally, the alkylation reactor is maintained at a feed inlet temperature and pressure suitable to facilitate the catalytic alkylation of aromatics present in the mixed effluent. The aromatics that are alkylated may be produced by aromatization that takes place in the activation reactor or may be a constituent of the hydrocarbon feed stream 301. These aromatics are alkylated by olefins that are largely produced by the activation of alkanes in the activation reactor. Alkylation of aromatics in the alkylation reactor produces an alkylation effluent comprising larger hydrocarbons comprising at least seven carbons that are preferably characterized by a boiling point that is in the boiling point range of a liquid transportation fuel (e.g., gasoline or diesel). Typically, the alkylation effluent comprises an increased percentage of alkylated aromatic compounds comprising from seven to nine carbon atoms. Optionally, the larger hydrocarbons also are characterized by a lower Reid vapor pressure and an increased octane rating.

The alkylation reactor is generally maintained at a pressure in a range from 14 psia to 800 psia, optionally in the range from 50 psia to 600 psia. The alkylation reactor is typically maintained at a temperature (generally measured within the alkylation reactor inlet) in a range from 150° C. to 350° C., optionally between 200° C. to 350° C. Typically, flow thorough the alkylation reactor is maintained at a weighted hourly space velocity (WHSV) in the range from 0.5 $hr^{-1}$ to 10 $hr^{-1}$ on an olefin basis. Optionally, the WHSV is in the range from 0.5 $hr^{-1}$ to 2.0 $hr^{-1}$. While higher overall throughput is desirable, ideally the chosen WHSV allows for conversion of at least 85% olefinic of hydrocarbons present in the mixed effluent at the selected operating temperature and pressure. The catalytic conversion occurring in the alkylation reactor produces an aromatic alkylation reactor effluent that typically comprises at least 30 wt. % (preferably, at least 40 wt %) of hydrocarbon molecules that are characterized by a boiling-point in the range of a liquid transportation fuel.

Speaking generally, the alkylation catalyst may comprise any catalyst characterized as either Brønsted or Lewis acidic. A wide variety of catalysts have been found to promote aromatic alkylation including, but not limited to, aluminum chloride, phosphoric acid, sulfuric acid, hydrofluoric acid, silica, alumina, sulfated zirconia, zeolites (including, for example, ZSM-5, ZSM-3, ZSM-4, ZSM-18, ZSM-20, zeolite-beta, H-Y, MCM-22, MCM-36 and MCM-49). In certain embodiments, the alkylation catalyst simultaneously promotes alkylation of aromatics and oligomerization of olefins present in the mixed effluent.

Referring again to the embodiment depicted in FIG. 3, the alkylation effluent 342 is conveyed to a first separator 345 that separates the alkylation effluent 342 into two fractions: a light hydrocarbons fraction 348 comprising C1-C4 hydrocarbons and $H_2$, and a condensed liquid hydrocarbons 352 comprising hydrocarbons containing at least five carbon atoms (C5+) that may be utilized directly as a blend component of a liquid transportation fuel or additionally processed prior to blending into a liquid transportation fuel. Preferably, the alkylation effluent comprises an increased quantity (or increased wt %) of alkylated aromatics containing from seven to nine carbon atoms. Preferably, these alkylated aromatics are monocyclic aromatic hydrocarbons.

In the embodiment depicted in FIG. 3, the condensed liquid hydrocarbons 352 is conveyed to a second separator 360 that is optionally a naphtha stabilizer. The second separator 360 is operable to remove a olefins fraction 367 (comprising predominantly alkanes and olefins containing four to six carbon atoms) from the condensed liquid hydrocarbons 352 in order to produce a liquid hydrocarbon product 363 that is characterized by at least one of a decreased Reid vapor pressure and increased octane rating, where the liquid hydrocarbon product 363 predominantly comprises hydrocarbons that are characterized by a boiling-point in the range of a liquid transportation fuel, such as, but not limited to, gasoline, diesel and jet fuel. The olefins fraction 367 may be used directly as a blend component 369 of a liquid transportation fuel or is optionally mixed with hydrocarbon feed stream 302 at a point that is downstream from the isomerization reactor 310. This recycling also serves as a route to indirectly recycle any benzene present in the olefins fraction to the alkylation reactor 340, as any such benzene would be relatively unreactive in the isomerization reactor 310 or activation reactor 320. Optionally, a portion of the mixed liquid hydrocarbons 331 derived from the condenser 330 may be combined with the liquid hydrocarbon product 363.

Speaking more generally, in certain embodiments the liquid hydrocarbon product may be hydrotreated in a hydrotreating reactor containing a hydrotreating catalyst in order to reduce olefin and aromatic content in the liquid hydrocarbon product, as well as to remove nitrogen-containing and sulfur-containing compounds. The hydrotreating reactor contains at least one hydrotreating catalyst (such as, for example, NiMo, CoMo, etc.) or a precious metal catalyst (such as Pt/$Al_2O_3$, Pd/$Al_2O_3$, or Pd/C, etc) and is maintained at a pressure and temperature suitable for facilitating hydrotreating catalytic reactions. Such processes are conventional in nature and therefore will not be described in greater detail here.

Again, referring to the embodiment depicted in FIG. 3, light hydrocarbons fraction 348 predominantly comprises hydrogen as well as C1-C4 hydrocarbons that were not converted in the alkylation reactor 340. Light hydrocarbons fraction 348 leaves the first separator 345 and is conveyed to a third separator 350 that utilizes a conventional separation technology (such as, but not limited to, pressure swing adsorption technology, membrane separation technology, etc.) to separate hydrogen from light hydrocarbons to produce a hydrogen stream and a C1-C4 light paraffins stream 355 that may be combusted 357 (not depicted) to provide at least a portion of the heat required for the process, or recycled to a point that is upstream from the activation catalyst 325 to serve as the diluent 316 that is mixed with the isomerization effluent 313

Certain embodiments comprise mixing a diluent with the isomerization effluent prior to contacting the resulting mixture with an activation catalyst. The diluent may be added in a ratio ranging from 10:1 to 1:10 molar ratio relative to the quantity of isomerization effluent fed to the activation reactor. The diluent may be added at any point that is upstream from, or within, the activation reactor, but prior to contacting the activation catalyst.

The diluent may comprise any substance that is less chemically-reactive than the constituents present in the isomerization effluent at the conditions of temperature and pressure that are maintained within the activation reactor. This is intended to prevent the diluent from reacting with the activation catalyst. Such properties are found in a large number of substances that are fully within the grasp of a person who is knowledgeable in the field. In certain embodiments, the diluent may comprise a C1-C4 light paraffins, including recycling C1-C4 light paraffins produced by the processes and systems described herein. In certain embodiments, the diluent may comprise any of methane, ethane, propane, butanes, benzene, toluene, xylenes, alkyl- or dialkyl-benzenes, naphthenes, C2-C5 olefins, and combinations thereof.

The presence of diluent during catalytic activation (i.e., activation) provides numerous advantages. First, it effectively decreases the concentration of the isomerization effluent within the activation reactor. This results in a small increase in the total conversion of alkanes to olefins or aromatics within the activation reactor. However, it also increases the selectivity toward the production of olefins, while slightly decreasing the selectivity toward the production of aromatics. Adjusting the ratio of diluent to isomerization effluent changes the ratio of olefins to aromatics in the resulting activation effluent, thereby providing a valuable point of operational control for downstream processes. Typically, the optimal molar production ratio of olefins to aromatics ranges from about 0.5:1 to about 1.5:1, in order to maximize the value captured in the olefin intermediates during the alkylation in the alkylation reactor. Mono-alkylated aromatics exhibit beneficial (increased) octane rating and vapor pressure for application as blending components in certain transportation fuels such as gasoline. In contrast, di-alkyl and tri-alkyl aromatics comprising more than nine carbon atoms are not well-suited for blending into gasoline, and exhibit nonoptimal cetane number for blending into diesel.

Addition of a diluent also advantageously favors the production of value-added olefins relative to C1-C4 light paraffins and also mitigates dimerization of C5 hydrocarbons to form durene (1,2,4,5-tetramethylbenzene), a byproduct notorious for precipitating as a solid from of gasoline blends.

EXAMPLES

The following examples are representative of certain embodiments of the inventive processes and systems disclosed herein. However, the scope of the invention is not intended to be limited to the embodiment specifically disclosed. Rather, the scope is intended to be as broad as is supported by the complete disclosure and the appending claims.

Example 1

This example demonstrates the preliminary rationale for isomerizing n-C5 to i-C5 in a hydrocarbon feed stream prior to contacting an activation catalyst. The graphs below illustrate differences in activation reactivity for n-C5 and i-C5. Feed streams were utilized that comprised either 100 wt. % i-C5 (i-C5) or 100 wt. % of n-C5 (n-C5). The catalyst was 1/8" extrudate consisting of 50 wt. % alumina binder and 50 wt. % ZSM-5 zeolite, and experiments were conducted at a WHSV of 1.3 hr$^{-1}$ at 1 atm. Results were averaged over the total time on stream of 16 hr.

Figure 4:
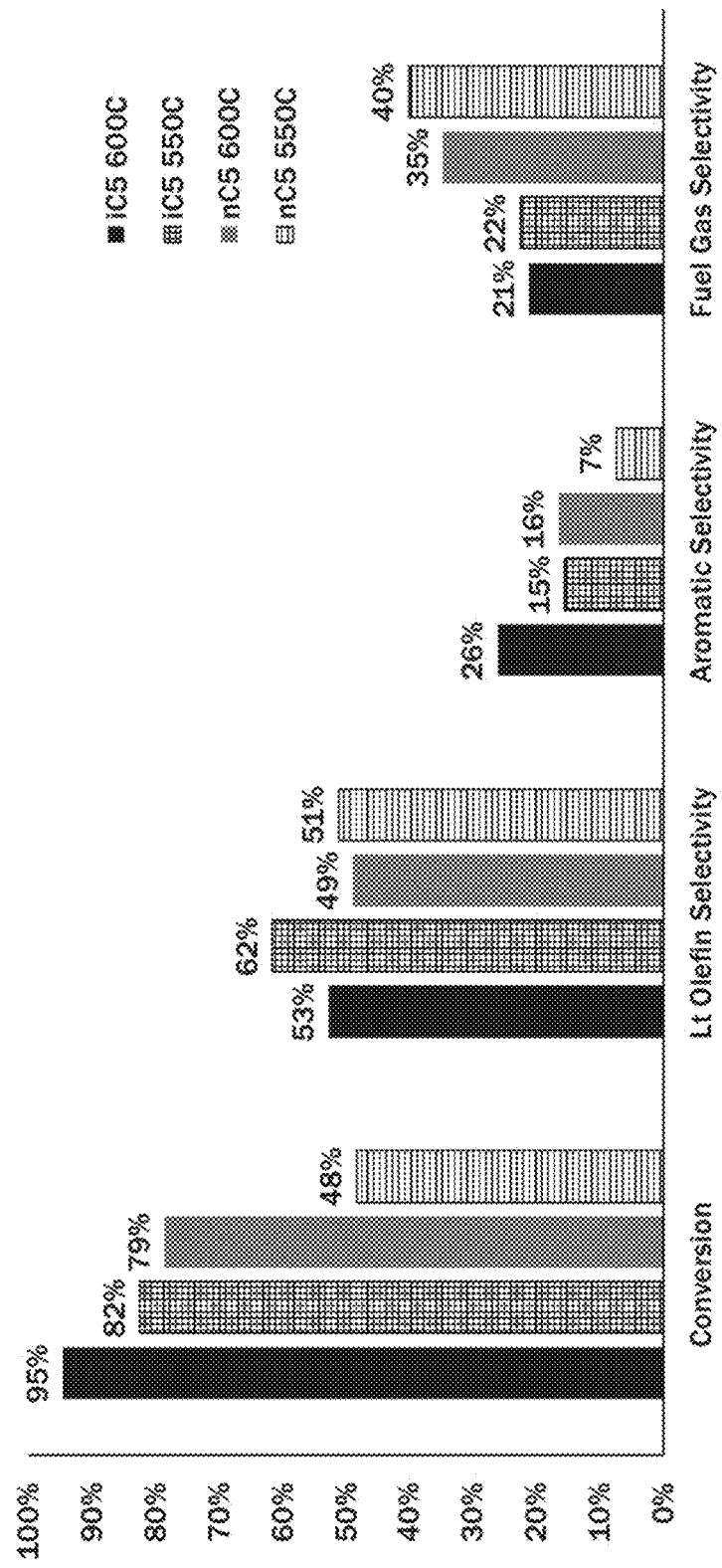
FIG. 4 is a bar graph depicting product selectivity resulting from catalytic activation of either n-pentane or iso-pentane at two different temperatures.
Figure 5:
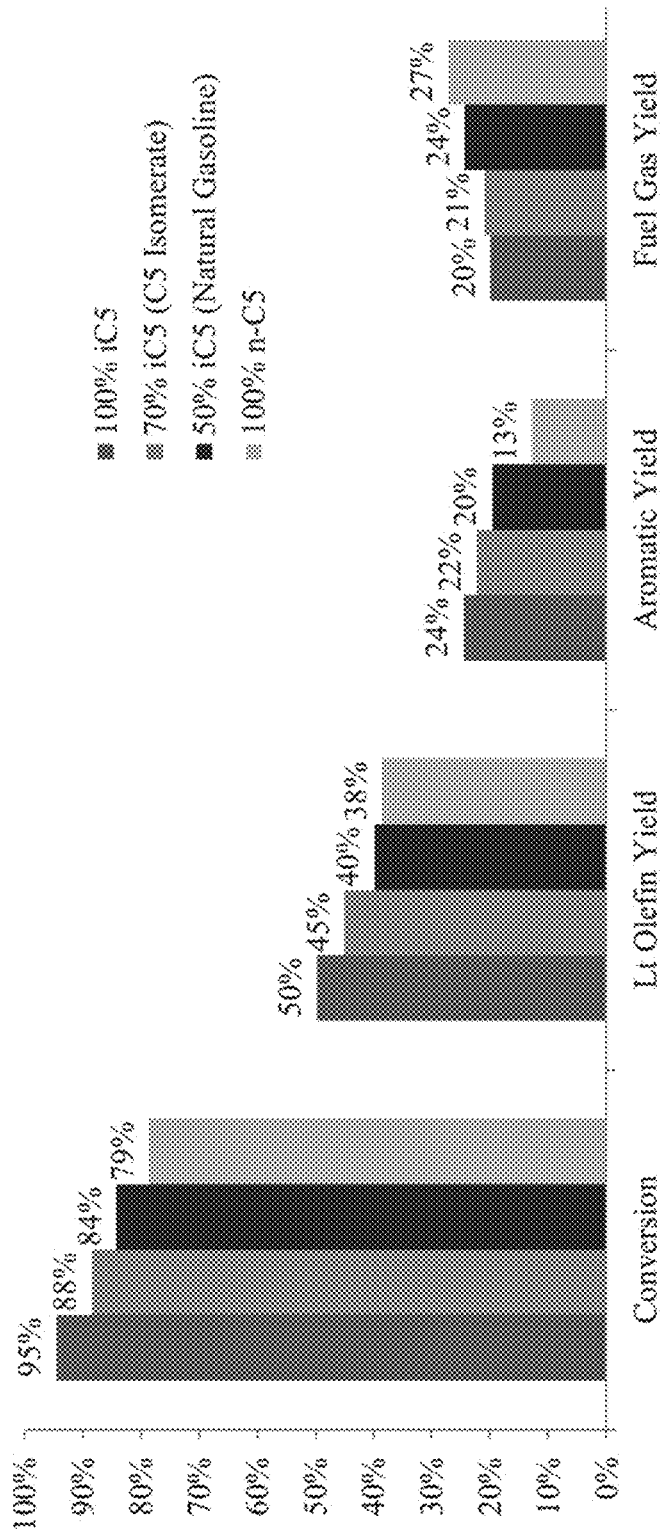
FIG. 5 is a bar graph showing the effect of isomerization of the feed stream on the total conversion and product yield for a first feed stream comprising a 1:1 ratio of n-C5 to i-C5, and a second feed stream comprising a 7:3 ratio of n-C5 to i-C5.
Figure 6:
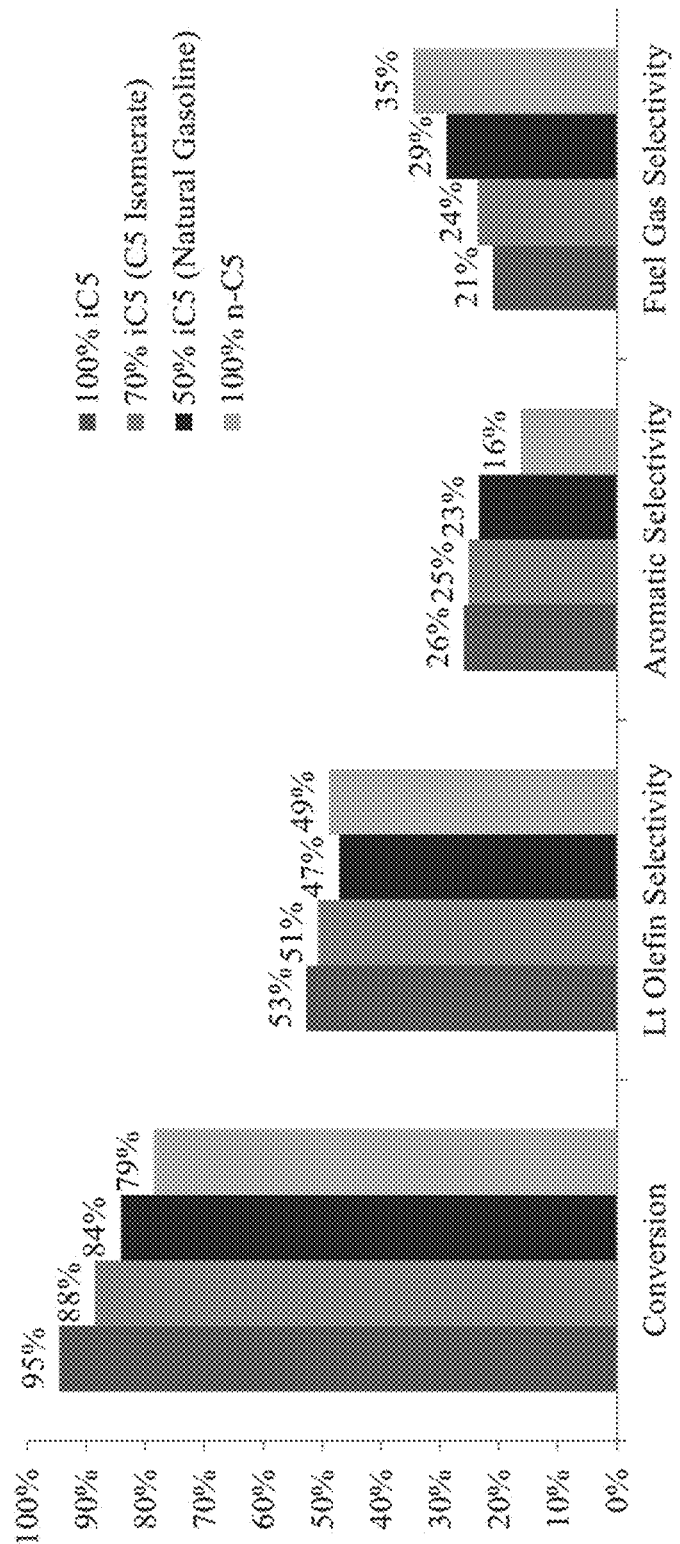
FIG. 6 is a bar graph showing the effect of isomerization of the feed stream on the total conversion and product selectivity for a first feed stream comprising a 1:1 ratio of n-C5 to i-C5, and a second feed stream comprising a 7:3 ratio of n-C5 to i-C5.

FIG. 4 is a bar graph depicting the results of catalytically activating each fraction at either 550° C. or 600° C. The graph depicts, as percentages, the total catalytic conversion of each feed stream (first column), the selectivity to light olefins as product (second column), the selectivity to aromatics as product (third column) and the selectivity to C1-C4 light paraffins (defined as non-olefin hydrocarbons containing from one to four carbon atoms), fourth column. Selectivity was calculated on a % carbon basis, relative to the portion of the feed stream fraction that was converted.

The results demonstrate that total conversion of a 100% n-C5 fraction at 600° C. was 79%, and a similar 82% conversion was observed when activating a 100% i-C5 feed stream at a 50° C. cooler temperature (i.e., 550° C.). Activating the i-C5 fraction at 550° C. (instead of 600° C.) also increased the selectivity towards the production of olefins while decreasing the selectivity of conversion toward aromatics. Lastly, these changes in selectivity caused no significant increase in the production of byproduct C1-C4 light paraffins. However, activation of n-C5 at 550° C. was generally unsuitable, and resulted in a 31% decrease in total conversion, and a noticeable increase in the production of C1-C4 light paraffins.

Example 2

This experiment demonstrates that isopentane (i-C5) is advantageously converted by both an activation catalyst and a subsequent oligomerization catalyst to produce a high percentage of product that is suitable for use as a liquid transportation fuel. A 100 wt. % i-C5 feed stream was upgraded by first contacting it with a zeolite activation catalyst, followed by contacting a zeolite oligomerization catalyst. Activation was conducted by contacting the feed stream with 1/8 in. diameter catalyst extrudate consisting of 50 wt. % alumina binder and 50 wt. % ZSM-5 zeolite catalyst at a temperature of 579° C., and a WHSV of 2.6 hr$^{-1}$ at 1 atm.

Oligomerization was conducted by contacting the activation effluent with a ZSM-5 zeolite catalyst in a reactor where the inlet temperature for the activation effluent was maintained at 250° C., the pressure was 1 atm, and the WHSV for the feed stream was 1.3 hr$^{-1}$. Results were time-averaged over 16 hours. The table shows the product distribution following conversion along with the selectivity to olefins and liquid product. The term "selectivity" indicates the percentage of the catalytically converted feed stream that was converted to a particular product.

TABLE 2

Upgrading pentanes by activation alone or activation plus oligomerization.

| | Activation | Activation + Oligomerization |
|---|---|---|
| Total Conversion (wt. %) | 88 | 87 |
| C1-C4 Light paraffins Yield | 32 | 32 |
| Upgraded Product Yield (wt. %) | 55 | 54 |
| Total Coke Yield (wt. %) | 0.1 | 0.1 |
| Light Olefin Yield (wt. %) | 42 | 16 |
| Light Olefin Selectivity (wt. %) | 48 | 19 |
| Liq. Yield (wt. %) | 13 | 38 |
| Liq. Product Selectivity (wt. %) | 15 | 44 |

The data in Table 2 show that the subjecting the effluent from the first activation reactor to a subsequent oligomerization step in a second reactor increased the liquid product yield from 13 wt. % to 38 wt. %. This liquid product yield represents a liquid product suitable for blending into a liquid transportation fuel such as gasoline (up from 13 wt. % prior to oligomerization), and that selectivity to liquid product for the portion of the feed stream that was converted was 44 wt. %. Undesirable C1-C4 light paraffins production was limited to 32 wt. % of the original feed stream, which optionally may be recycled to be either activated or to serve as a diluent in at least one of the activation reactors. Further, the final product only comprised 16 wt. % of light olefins, (primarily ethylene), which may be recycled to the process, or diverted to be utilized in any of a variety of conventional processes.

Example 3

This experiment demonstrates that isopentane (i-C5) is advantageously converted by both an activation catalyst and a subsequent alkylation catalyst to produce a high percentage of product that is suitable for use as a liquid transportation fuel. A 100 wt. % i-C5 feed stream was upgraded by first contacting it with a zeolite activation catalyst, followed by contacting the activation effluent with a zeolite alkylation catalyst. Activation was conducted by contacting the feed stream with a 1/8 in. diameter catalyst extrudate consisting of 50 wt. % alumina binder and 50 wt. % ZSM-5 zeolite catalyst in an activation reactor. The temperature of the activation reactor at the inlet for the feed stream was 579° C., the pressure was 1 atm, and the WHSV for the feed stream was 2.6 hr$^{-1}$. Alkylation was then conducted by contacting the effluent with a ZSM-5 catalyst in a reactor where the temperature at the inlet for the feed stream was 230° C. and the WHSV of the feed stream was 1.3 hr$^{-1}$ at 1 atm. Results were time-averaged over 16 hours. The table shows the product distribution following conversion along with the selectivity to olefins and liquid product. The term "selectivity" indicates the percentage of the catalytically converted feed stream that was converted to a particular product.

TABLE 3

Upgrading isopentane by activation only or activation followed by alkylation.

| | Activation | Activation + Alkylation |
|---|---|---|
| Total Conversion (wt. %) | 87 | 87 |
| Light paraffins Yield (wt. %) | 32 | 32 |
| Upgraded Product Yield (wt. %) | 55 | 55 |
| Total Coke Yield (wt. %) | 0.1 | 0.2 |

TABLE 3-continued

Upgrading isopentane by activation only or activation followed by alkylation.

|  | Activation | Activation + Alkylation |
|---|---|---|
| Light Olefin Yield (wt. %) | 42 | 12 |
| Light Olefin Selectivity (wt. %) | 48 | 14 |
| Liquid Yield (wt. %) | 13 | 42 |
| Liquid Product Selectivity (wt. %) | 15 | 48 |

The data in Table 3 show that subjecting the activation effluent to a subsequent alkylation step increased the liquid product yield from 13 wt. % to 42 wt. %. This liquid product is suitable for blending into a liquid transportation fuel such as gasoline, and possesses an increased research octane number, a suitable distillation T50 and endpoint, and low vapor pressure. Selectivity to liquid product for the portion of the feed stream that was converted increased from 15 wt. % to 48 wt. %. Undesirable C1-C4 light paraffins production was limited to 32 wt. % of the original feed stream. Further, the final product only comprised 14 wt. % of light olefins. These olefins may be recycled to the activation reactor, used as a diluent in the alkylation reactor, or diverted to be utilized in any of a variety of conventional processes.

Note that the results shown in the above table may underestimate the total percentage of a mixed pentanes feed stream that would be available for blending into a liquid transportation fuel, as a typical hydrocarbon feed stream (such as, but not limited to, natural gasoline) may also include an excess quantity of C5/C6+ that would not be either catalytically cracked or introduced into the alkylation reactor. This excess quantity of C5/C6+ is suitable for direct blending into the liquid hydrocarbon product. In certain embodiments, a portion of the nC5/C6+ fraction is diverted when necessary to achieve the desired 0.5:1 to 1.5:1 olefin to aromatic ratio that maximizes production of mono-alkylated aromatics in the alkylation reactor.

Example 4

Preliminary experimentation revealed that contacting a simulated natural gasoline feed stream (containing approximately 1:1 ratio of n-C5:i-C5) with an isomerization catalyst in a single pass increases the ratio of i-C5 to n-C5 to approximately 7:3. An experiment was next performed to assess potential differences in conversion yield and selectivity to various products when a feed stream comprising a simulated isomerization effluent (7:3 ratio of i-C5 to n-C5) was contacted with an activation catalyst comprising an ⅛" extrudate consisting of 50 wt. % alumina binder and 50 wt. % ZSM-5 zeolite. The reaction was conducted at 600° C., with a flow rate of 5.0 hr$^{-1}$, for a total of 16.5 hr. on stream, and produced an effluent comprising light olefins, aromatics and light paraffins. The averaged results are shown in Table 4, below:

TABLE 4

ZSM-5 activation and conversion of several feed streams comprising different amounts of n-pentane (n-C5) and isopentane (i-C5) isomers.

|  | 100 wt. % iC5 | 100 wt. % n-C5 | 70 wt. % i-C5 30 wt. % n-C5 | 50 wt. % i-C5 50 wt % n-C5 |
|---|---|---|---|---|
| Material Balance | 93% | 104% | 84% | 101% |
| Conversion | 95% | 79% | 88% | 84% |
| Fuel gas yield | 20% | 27% | 21% | 24% |
| Product Yield | 74% | 51% | 67% | 59% |
| Coke Yield | 0% | 0% | 0% | 0% |
| Lt Olefin Yield | 50% | 38% | 45% | 40% |
| Lt Olefin Selectivity | 53% | 49% | 51% | 47% |
| Aromatic Yield | 24% | 13% | 22% | 20% |
| Aromatic Selectivity | 26% | 16% | 25% | 23% |
| Fuel Gas Yield | 20% | 27% | 21% | 24% |
| Fuel Gas Selectivity | 21% | 35% | 24% | 29% |

The results clearly indicate that increasing the percentage of i-C5 in the feed resulted in a significant increase in both olefin yield (+5%) and selectivity (+4%), and a lesser increase in both aromatic yield (+2%) and selectivity (+2%). Simultaneously, selectivity to fuel gas was advantageously decreased by 5%.

Example 5

This experiment demonstrates the effect that a methane diluent has on catalytic activation and conversion of two different hydrocarbon feed streams: 1) a simulated "natural gasoline" comprising 50 wt. % i-C5 and 50 wt. % n-C5 isomers, and 2) a simulated "isomerization effluent" comprising 70 wt. % i-C5 and 30 wt. % n-C5. Each of the two feed streams were fed at a WHSV of 1.3 hr$^{-1}$ to a reactor containing an activation catalyst comprising a ⅛" extrudate consisting of 50 wt. % alumina binder and 50 wt. % ZSM-5 zeolite. The temperature of the reactor (at the inlet for the feed stream) was maintained at 600° C. and 20 psig (2.4 Bar) and results were time-averaged for 16.5 hr. For certain reactions, methane diluent was co-fed along with each feed stream at a methane:feed stream molar ratio of 2:1.

The reaction produced an effluent comprising light olefins, aromatics and light paraffins. Table 5 (below) shows the effect of the methane diluent on the total conversion of the 1:1 and 7:3 feed streams, respectively, as well as the selectivity of each conversion toward light olefins, aromatics, and byproduct C1-C4 fuel gas.

TABLE 5

Catalytic activation of a 1:1 i-C5:n-C5 feed stream and a 7:3 1 i-C5:n-C5 feed stream in both the absence and presence of methane diluent.

|  | Feed Stream | | | |
|---|---|---|---|---|
|  | 1:1 i-C5:n-C5 | 1:1 i-C5:n-C5 | 7:3 1 i-C5:n-C5 | 7:3 1 i-C5:n-C5 |
|  |  | +/− Diluent | | |
|  | No Diluent | CH$_4$ Diluent | No Diluent | CH$_4$ Diluent |
| Material Balance | 101% | 103% | 102% | 101% |
| Conversion | 92% | 80% | 93% | 81% |
| Fuel gas yield | 37% | 22% | 34% | 21% |
| Product Yield | 54% | 58% | 58% | 60% |
| Coke Yield | 0% | 0% | 0% | 0% |

TABLE 5-continued

Catalytic activation of a 1:1 i-C5:n-C5 feed stream and a 7:3 1 i-C5:n-C5 feed stream in both the absence and presence of methane diluent.

| | Feed Stream | | | |
|---|---|---|---|---|
| | 1:1 i-C5:n-C5 | 1:1 i-C5:n-C5 +/− Diluent | 7:3 1 i-C5:n-C5 | 7:3 1 i-C5:n-C5 |
| | No Diluent | CH₄ Diluent | No Diluent | CH₄ Diluent |
| Lt. Olefin Yield | 34% | 44% | 35% | 43% |
| Lt. Olefin Selectivity | 37% | 55% | 38% | 53% |
| Aromatic Yield | 20% | 14% | 22% | 17% |
| Aromatic Selectivity | 21% | 17% | 24% | 21% |
| Fuel Gas Yield | 37% | 22% | 34% | 21% |
| Fuel Gas Selectivity | 41% | 27% | 37% | 26% |

The data in Table 5 indicate that adding inert diluent caused slight loss of overall conversion, but significantly increased the yield and selectivity to light olefin production for both the 1:1 and 7:3 feed streams. Adding inert diluent also greatly diminished selectivity to production of C1-C4 fuel gas. Meanwhile, only a small drop in selectivity to aromatics production was observed for the 1:1 ratio feed stream in the presence of diluent, which was offset by an equivalent increase in aromatics production in the 7:3 ratio feed stream (in the presence of diluent). All of these results are advantageous to the process, particularly in certain embodiments where the mixed effluent is immediately utilized as feed stream for either an oligomerization or alkylation process. In certain embodiments that comprise an oligomerization process, diluent is added to the activation feed stream at a ratio that maximizes light olefin production, providing an advantageous feed stream for the oligomerization catalyst. In certain embodiments that comprise an aromatic alkylation process, diluent can be added to the activation feed stream at a ratio that produces a first effluent comprising olefins and aromatics at a ratio (typically between 0.5:1 and 1.5:1 by mole) that provides an advantageous feed stream for an aromatic alkylation process.

In closing, it should be noted that the discussion of any reference is not an admission that it is prior art to the present disclosure, in particular, any reference that may have a publication date after the priority date of this application. Although the systems and processes described herein have been described in detail, it is understood that various changes, substitutions, and alterations can be made without departing from the spirit and scope of the invention as defined by the following claims.

Definitions

In the present disclosure, the term "conversion" is defined as any of the chemical reactions that occur during upgrading of hydrocarbons to liquid transportation fuels. Examples of such reactions include, but are not limited to: oligomerization, aromatization, dehydrogenation, alkylation, hydrogenation and cracking.

We claim:

1. A method for converting a feed stream comprising pentanes to produce liquid hydrocarbons comprising monocyclic aromatics, comprising:
    a. providing a hydrocarbon feed stream comprising at least 50 wt. % pentanes, including both n-pentane and isopentane;
    b. contacting the hydrocarbon feed stream with one or more isomerization catalysts in a first reaction zone that is maintained at a temperature and a pressure that facilitates isomerization of at least a portion of the n-pentane in the hydrocarbon feed stream to isopentane, thereby producing an isomerization effluent characterized by an increased ratio of isopentane to n-pentane relative to the hydrocarbon feed stream;
    c. contacting the isomerization effluent with an activation catalyst in a second reaction zone that is maintained at a temperature and pressure that facilitates at least one reaction selected from dehydrogenation, cracking and aromatization, thereby converting at least a portion of hydrocarbons present in the isomerization effluent to produce an activation effluent comprising olefins containing from two to five carbon atoms, monocyclic aromatics and unconverted alkanes containing from two to five carbon atoms; and
    d. at least partially condensing the activation effluent to produce a liquid hydrocarbons fraction and a gaseous light hydrocarbons fraction, wherein the liquid hydrocarbons fraction comprises monocyclic aromatics and unreacted alkanes containing at least five carbon atoms, wherein the gaseous light hydrocarbons fraction comprises at least 80 wt. % hydrocarbons containing four or fewer carbon atoms and hydrogen.

2. The method of claim 1, further comprising separating the liquid hydrocarbons fraction into an aromatics fraction and an unreacted C5/C6 hydrocarbons fraction, wherein the aromatics fraction comprises monocyclic aromatics suitable for use as a blend component of gasoline and the unreacted C5/C6 hydrocarbons fraction comprises alkanes and olefins containing from five to six carbons that is optionally mixed with the hydrocarbon feed stream of part a).

3. The method of claim 1, wherein the hydrocarbon feed stream comprises at least 5 wt. % of hydrocarbons containing four or fewer carbon atoms.

4. The method of claim 1, wherein the hydrocarbon feed stream comprises at least 60 wt. % pentanes.

5. The method of claim 1, wherein the activation catalyst comprises one or more zeolites characterized by Si/Al ratio ranging from 12 to 80.

6. The method of claim 1, wherein the activation catalyst comprises ZSM-5 zeolite.

7. The method of claim 1, wherein the activation catalyst facilitates at least one reaction selected from the group consisting of oligomerization, dehydrogenation, and aromatization.

8. The method of claim 1, wherein the first reaction zone is maintained at a temperature in a range from 500° C. to 625° C. and a pressure in the range from 15 psig to 100 psig.

9. The method of claim 8, wherein the diluent is added in an amount that alters the specificity of the activation catalyst to increase the production of olefins, decrease the production of aromatics, or combinations thereof, thereby increasing a ratio of olefins to aromatics in the activation effluent.

10. The method of claim 8, wherein the diluent is added in an amount that is effective to produce an activation effluent characterized by an olefins to aromatics ratio in a range of 0.5 to 2.0.

11. The method of claim 8, wherein the diluent is added in an amount that is effective to produce an activation effluent characterized by an olefins to aromatics ratio in a range of 0.5 to 1.0.

12. The method of claim 8, wherein the diluent is selected from methane, ethane, propane, butanes, and combinations thereof.

13. The method of claim 1, wherein the temperature in the first reaction zone is maintained at a temperature in a range from 525° C. to 600° C. and a pressure in the range from 15 psig to 75 psig.

14. The method of claim 1, wherein the second reaction zone is maintained at a temperature in a range from 550° C. to 600° C. and a pressure in the range from 20 psig to 60 psig.

15. The method of claim 1, wherein the second reaction zone is maintained at a temperature in a range from 575° C. to 600° C. and a pressure in the range from 20 psig to 50 psig.

16. The method of claim 1, further comprising adding a diluent to at least one of the hydrocarbon feed stream and the isomerization effluent prior to the contacting with the activation catalyst, wherein the diluent is characterized as less likely to react with the activation catalyst than the hydrocarbon feed stream at the conditions of temperature and pressure that are maintained in the first reaction zone, and wherein the diluent is characterized as less likely to react with the activation catalyst than molecules present in the isomerization effluent at the conditions of temperature and pressure that are maintained in the second reaction zone.

17. The method of claim 1, further comprising adding a diluent to at least one of the hydrocarbon feed stream and the isomerization effluent prior to the contacting with the activation catalyst, wherein the diluent does not react with the isomerization catalyst at the conditions of temperature and pressure that are maintained in the first reaction zone, and wherein the diluent does not react with the activation catalyst at the conditions of temperature and pressure that are maintained in the second reaction zone.

18. The method of claim 1, wherein the hydrocarbon feed stream is contacted with one or more isomerization catalysts contained within in multiple reaction zones that are arranged in a series configuration.

\* \* \* \* \*